United States Patent
Borries et al.

(10) Patent No.: US 9,451,969 B2
(45) Date of Patent: Sep. 27, 2016

(54) FEMORAL REAMERS HAVING A WEAR INDICATOR AND RELATED KITS AND METHODS

(71) Applicant: Zimmer, Inc., Warsaw, IN (US)

(72) Inventors: Paul Borries, Columbia City, IN (US); Bart C. Benedict, Warsaw, IN (US); Trent Pals, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 14/787,850

(22) PCT Filed: May 15, 2014

(86) PCT No.: PCT/US2014/038197
§ 371 (c)(1),
(2) Date: Oct. 29, 2015

(87) PCT Pub. No.: WO2014/186576
PCT Pub. Date: Nov. 20, 2014

(65) Prior Publication Data
US 2016/0074045 A1 Mar. 17, 2016

Related U.S. Application Data

(60) Provisional application No. 61/824,192, filed on May 16, 2013.

(51) Int. Cl.
*A61B 17/16* (2006.01)
(52) U.S. Cl.
CPC ......... *A61B 17/1668* (2013.01); *A61B 17/164* (2013.01); *B23B 2260/144* (2013.01)
(58) Field of Classification Search
CPC ............ A61B 17/164; A61B 17/1668; B23B 2260/144
See application file for complete search history.

(56) References Cited

U.S. PATENT DOCUMENTS

| 2003/0103823 A1 | 6/2003 | Hauptmann et al. |
| 2005/0025928 A1 | 2/2005 | Annanolli et al. |
| 2005/0282112 A1* | 12/2005 | Kumar ..................... A61C 3/02 433/141 |

(Continued)

FOREIGN PATENT DOCUMENTS

WO WO-2014186576 A1 11/2014

OTHER PUBLICATIONS

"International Application Serial No. PCT/US2014/038197, International Search Report mailed Aug. 21, 2014", 5 pgs.

(Continued)

*Primary Examiner* — Andrew Yang
(74) *Attorney, Agent, or Firm* — Schwegman Lundberg & Woessner, P.A.

(57) ABSTRACT

A femoral reamer (100) can include a base material (304) and a coating (302) disposed on the base material. The coating can be harder than the base material and, as a result, the femoral reamer can wear more slowly than if the coating was absent. The coating can be a different color than the base material. When the coating is worn off, such wear can be easily observed from a visual inspection of the femoral reamer. The coating can have an initial thickness (i.e., a thickness prior to use) that is related to a tolerance on a size and/or a shape of a hole drilled by the femoral reamer. When the coating is worn off, the size and/or the shape of the hole drilled by the femoral reamer may be at or near an edge of a specified tolerance range. The femoral reamer can be part of a kit and a method.

20 Claims, 6 Drawing Sheets

(56) References Cited

U.S. PATENT DOCUMENTS

| | | | |
|---|---|---|---|
| 2006/0269901 A1* | 11/2006 | Rosenblood | A61C 1/07 433/166 |
| 2009/0004440 A1 | 1/2009 | Ban et al. | |
| 2012/0259338 A1 | 10/2012 | Carr et al. | |

OTHER PUBLICATIONS

"International Application Serial No. PCT/US2014/038197, Written Opinion mailed Aug. 21, 2014", 6 pgs.

* cited by examiner

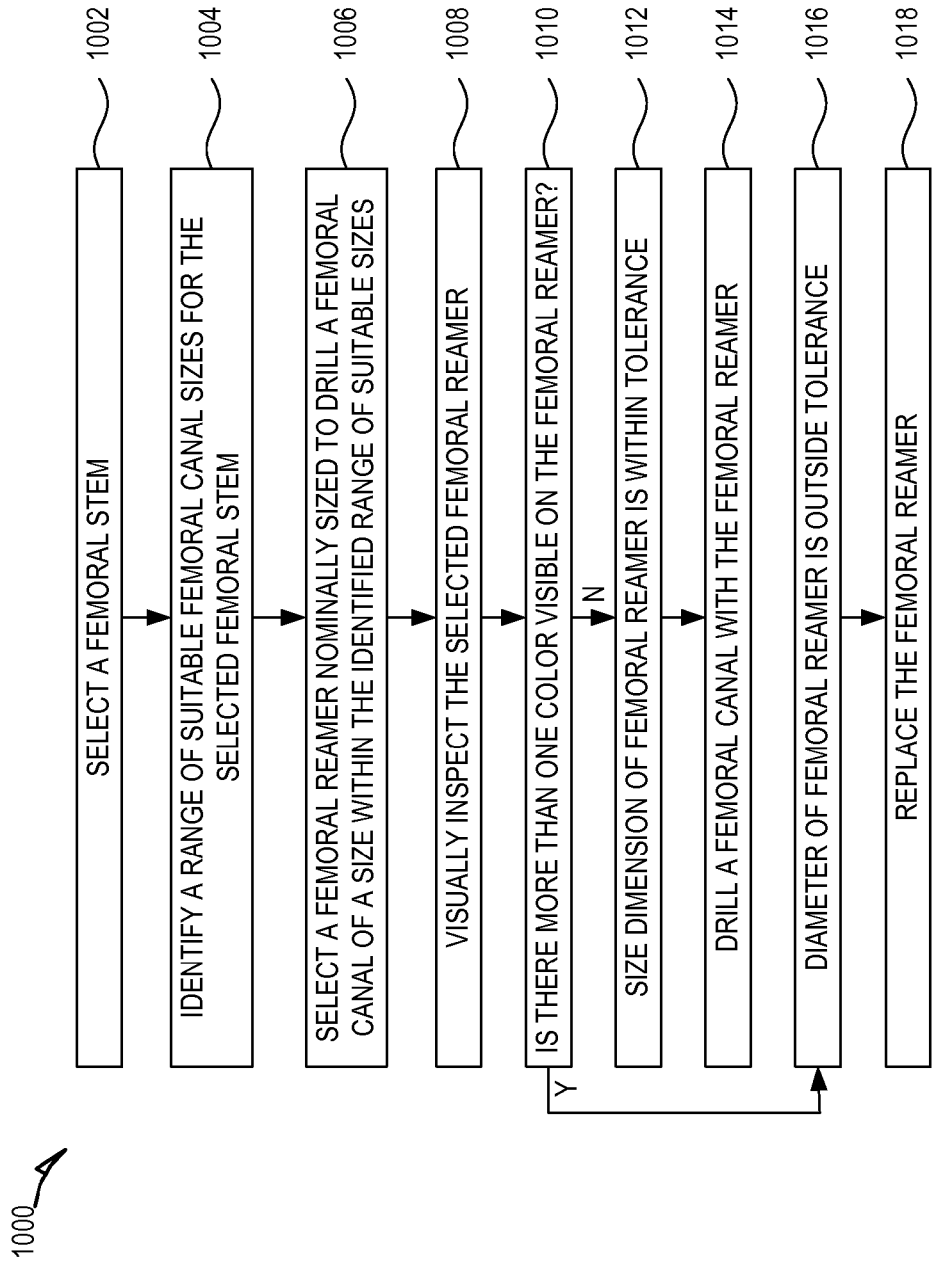

FEMORAL REAMERS HAVING A WEAR INDICATOR AND RELATED KITS AND METHODS

CLAIM OF PRIORITY

This application is a U.S. national stage filing under 35 U.S.C. 371 from International Application No. PCT/US2014/038197, filed on May 5, 2014, and published as WO 2014/186576 A1 on Nov. 20, 2014, which claims the benefit of U.S. Provisional Patent Application Ser. No. 61/824,192, filed on May 16, 2013, the benefit of priority of each of which are claimed hereby, and which are incorporated by reference herein in their entirety.

BACKGROUND

A human hip joint connects a femur (sometimes referred to as a thigh bone) to an acetabulum (sometimes referred to as a hip socket) of the pelvis. The hip joint supports the weight of the body and is important for retaining balance. Some types of injury, disease, or degeneration can produce pain and/or restricted motion in the hip joint. One treatment for certain types of damage to a hip joint is surgery. For relatively mild hip damage, the hip may be repaired. For more severe damage, the hip may be replaced.

In many types of hip replacement surgery, a portion of the femur is reamed or drilled to form a femoral canal, and a femoral stem is implanted within the femoral canal. Femoral stems are available in a variety of shapes, lengths, tapers, bevels, and cross-sectional shapes. A practitioner typically chooses a particular femoral stem to best fit a patient's anatomy and to address the specific requirements of a patient's treatment. The femoral stem may be cemented in place, or may alternatively be held in place by a press-fit and subsequent bone growth that encompasses the stem or bonds to the stem.

OVERVIEW

The present inventors recognize that it is important for a femoral canal to be drilled or reamed precisely to a particular size and/or a particular shape, in order to ensure a tight fit between a femur and an implanted femoral stem.

A practitioner drills the femoral canal with a femoral reamer. A femoral reamer performs a similar function as a drill bit, and is often used with a mechanized drill to rotate the femoral reamer about its longitudinal axis. Femoral reamers can be presented to a practitioner in the form of a kit, which can include femoral reamers having various sizes and shapes. The femoral reamers in the kit can be matched to respective configurations of the femoral stem. Femoral reamers are typically used repeatedly, so that after a femoral reamer is used for a procedure, the reamer is cleaned, sterilized, and returned to the kit or surgical room for subsequent use.

The present inventors further recognize that over the course of multiple uses, a femoral reamer may become worn. The wear may affect the profile and/or the diameter of a hole drilled by the femoral reamer. For instance, a femoral canal drilled with a worn femoral reamer may have a diameter that is slightly too small, which is undesirable and can lead to improper fitting of the femoral stem. A worn reamer may also become dull, making the femoral preparation more difficult.

It is generally impractical to test the femoral reamers for wear. Such testing is time-consuming and expensive. Furthermore, if a femoral reamer were to be tested after each use, it would require that the femoral reamer be cleaned twice for each use—once after the surgical use but before testing, and once after testing but before insertion back into the kit.

For at least the above reasons, there exists a need for quickly and easily determining an amount of wear on a femoral reamer.

A femoral reamer can include a base material and a coating disposed on the base material. The coating can be harder than the base material and, as a result, the femoral reamer can wear more slowly than if the coating was absent and the base material was exposed during use. The coating can be a different color than the base material, so that when the coating is worn off from a region on the femoral reamer, such wear can be easily observed from a visual inspection of the femoral reamer. The coating can have an initial thickness, prior to use, that is related to a tolerance on a size and/or a shape of a hole drilled by the femoral reamer and/or a prescribed sharpness. When the coating is worn off, the size of the hole drilled by the femoral reamer may be at or near an edge of a specified tolerance range, or the blades on the femoral reamer may be dull. The femoral reamer can be part of a kit and a method.

To further describe the present methods, kits, and femoral reamers, a non-limiting list of examples is provided here:

In Example 1, the method can include selecting a femoral stem. A range of suitable femoral canal sizes can be identified for the selected femoral stem to be implanted. A femoral reamer can be selected including a base material of a first color and a coating of a second, different color. The selected femoral reamer can be nominally sized to drill a femoral canal of a size within the identified range of suitable femoral canal sizes. The selected femoral reamer can be visually inspected. At least one area can be observed on the selected femoral reamer in which the first color of the base material is visible through the second color of the coating. It can be determined from the observed at least one region, that the selected femoral reamer has a size dimension that is outside the identified range of suitable femoral canal sizes.

In Example 2, the method of Example 1 can optionally be configured such that selecting the femoral reamer can include selecting a femoral reamer including a coating having a thickness related to the identified range of suitable femoral canal sizes.

In Example 3, the method of any one or any combination of Examples 1 or 2 can optionally be configured such that selecting the femoral reamer can include selecting a femoral reamer including a coating having a thickness equal to half of a width of the identified range of suitable femoral canal sizes.

In Example 4, the method of any one or any combination of Examples 1-3 can optionally be configured such that selecting the femoral reamer can include selecting a femoral reamer including a coating that is harder than the base material.

In Example 5, the method of any one or any combination of Examples 1-4 can optionally be configured such that selecting the femoral reamer can include selecting a desired combination of a shaft, an elongate body disposed at a distal end of the shaft, and a plurality of blades disposed helically around an exterior of the elongate body.

In Example 6, the method of any one or any combination of Examples 1-5 can optionally be configured such that selecting the desired combination can include selecting a plurality of blades that extend less than a full revolution around the elongate body.

In Example 7, the method of any one or any combination of Examples 1-6 can optionally be configured such that selecting the desired combination can include selecting a plurality of blades having the coating disposed over an outer blade surface and between adjacent blades in the plurality.

In Example 8, the method can include selecting a femoral stem to be implanted. A range of suitable femoral canal sizes can be identified for the selected femoral stem. A femoral reamer can be selected from a kit of differently-sized femoral reamers including a base material of a first color and a coating f a second, different color. The selected femoral reamer can be nominally sized to drill a femoral canal of a size within the identified range of suitable femoral canal sizes. The selected femoral reamer can be visually inspected. At least one area can be observed on the selected femoral reamer in which the base material of the femoral reamer is visible through the coating on the femoral reamer. It can be determined from the observed that at least one area that the selected femoral reamer has a sixe dimension that is outside the identified range of suitable femoral canal sizes.

In Example 9, the method of Example 8 can optionally be configured such that selecting the femoral reamer can include selecting a femoral reamer including a coating having a thickness related to the identified range of suitable femoral canal sizes.

In Example 10, the method of any one or any combination of Examples 8 or 9 can optionally be configured such that selecting the femoral reamer can include selecting a femoral reamer including a coating having a thickness equal to half of a width of the identified range of suitable femoral canal sizes.

In Example 11, the method of any one or any combination of Examples 8-10 can optionally be configured such that selecting the femoral reamer can include selecting a femoral reamer including a coating that is harder than the base material.

In Example 12, the method of any one or any combination of Examples 8-11 can optionally be configured such that selecting the femoral reamer can include selecting a desired combination of a shaft, an elongate body disposed at a distal end of the shaft, and a plurality of blades disposed helically around an exterior of the elongate body.

In Example 13, the method of any one or any combination of Examples 8-12 can optionally be configured such that selecting the desired combination can include selecting a plurality of blades that extend less than a full revolution around the elongate body.

In Example 14, the method of any one or any combination of Examples 8-13 can optionally be configured such that selecting the desired combination can includes selecting a plurality of blades having the coating disposed over an outer blade surface and between adjacent blades in the plurality.

In Example 15, a femoral reamer kit can include a plurality of femoral reamers corresponding to a plurality of femoral stem configurations. Each femoral stem configuration can have an associated specified femoral canal size and a specified tolerance on the specified femoral canal size. Each femoral reamer can include a shaft, an elongate body disposed at a distal end of the shaft, and a plurality of blades disposed helically around an exterior of the elongate body. Each elongate body can include a base material of a first color and a coating of s second, different color disposed on the base material. The coating can be harder than the base material. The coating can have a thickness related to the specified tolerance on the specified femoral canal size.

In Example 16, the femoral reamer kit of Example 15 can optionally be configured such that the specified tolerance on the specified femoral canal size can be different for at least two of the femoral stem configurations in the plurality. The coating thickness can be different for at least two of the femoral reamers in the plurality.

In Example 17, the femoral reamer kit of any one or any combination of Examples 15 and 16 can optionally be configured such that the base material can be the same for all the femoral reamers in the plurality. The coating can be the same material for all the femoral reamers in the plurality.

In Example 18, the femoral reamer kit of any one or any combination of Examples 15-17 can optionally be configured such that for at least one of the femoral reamers in the plurality, the thickness of the coating can equal half the width of the specified tolerance on the specified femoral canal size.

In Example 19, the femoral reamer kit of any one or any combination of Examples 15-18 can optionally be configured such that for at least one of the femoral reamers in the plurality, the coating is disposed over the plurality of blades and between adjacent blades in the plurality.

In Example 20, the femoral reamer kit of any one or any combination of Examples 15-19 can optionally be configured such that for at least one of the femoral reamers in the plurality, each blade in the plurality extends less than a full revolution around the elongate body.

Each of these non-limiting examples can stand on its own, or can be combined in various permutations or combinations with one or more of the other examples.

This Overview is intended to provide examples of subject matter of the present patent document. It is not intended to provide an exclusive or exhaustive explanation of the invention. The Detailed Description below is included to provide further information about the present patent document.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present patent document.

FIG. 10 is a flow chart of an inspection process for a femoral reamer.

DETAILED DESCRIPTION

Figure 1:
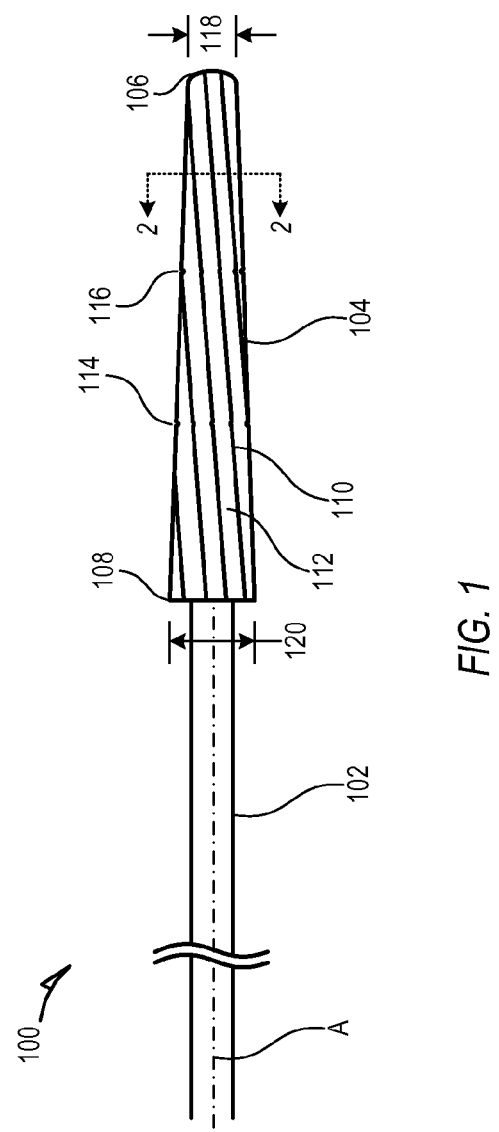
FIG. 1 is a side-view drawing of an example femoral reamer.

FIG. 1 is a side-view drawing of an example femoral reamer 100. The femoral reamer 100 includes an elongated shaft 102 having a longitudinal axis (A). A proximal end (not shown) of the shaft 102 may include a handle or may include a mechanism to removably couple the shaft 102 to a mechanical drill. The shaft 102 extends distally from the proximal end.

An elongate body 104 is disposed at a distal end of the shaft 102. In some examples, the elongate body 104 is longitudinally tapered so that a distal end 106 of the elongate body 104 has a distal diameter 118, and a proximal end 108 of the elongate body 104 has a proximal diameter 120 greater than the distal diameter. In some examples, the taper has a particular angular value, such as 3.5 degrees. In other examples, the elongate body 104 has no taper so that its distal diameter 118 and its proximal diameter 120 are equal. In some examples, the proximal diameter 120 is greater than a diameter of the shaft 102.

One or more blades 110 can extend helically around the exterior of the elongate body 104. In some examples, the elongate body 104 includes a single blade 110 that extends more than one revolution around the elongate body 104. In other examples, the elongate body 104 includes multiple blades 110 that extend more than one revolution around the elongate body 104. In still other examples, such as the configuration shown in FIG. 1, the elongate body 104 includes multiple blades 110 that all extend less than one revolution around the elongate body 104. The blades 110 extend radially outward farther than areas 112 on the elongate body 104 located between the blades 100. As the elongate body 104 is rotated around its longitudinal axis (A), the blades 110 contact bone material of the femur.

One or more optional indentations 114, 116 can extend inwardly at respective locations along the longitudinal axis (A). These indentations 114, 116 provide a visual indication of the depth of the hole drilled by the femoral reamer 100. In some examples, the indentations 114, 116 are spaced apart by a specified length, such as an inch or a centimeter.

Figure 2:
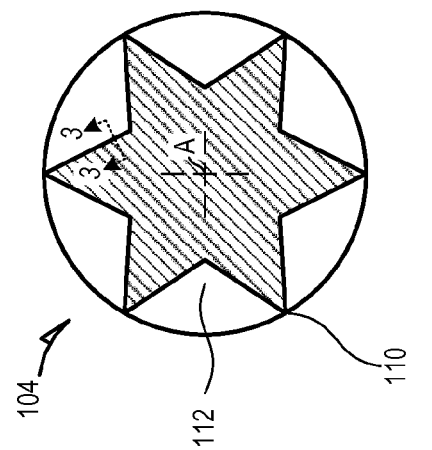
FIG. 2 is an end-on cross-sectional drawing of the femoral reamer of FIG. 1.

FIG. 2 is an end-on cross-sectional drawing of the femoral reamer 100 of FIG. 1. The cross-sectional view of FIG. 2 shows the blades 110 extending radially outward farther than the areas 112 between the blades 110.

In the example of FIG. 2, the shape of the blades 110 is symmetric and sharply peaked. There are many other possible configurations for the blade shape, including asymmetric configurations that can favor one of the two directions of rotation around the longitudinal axis (A) and rounded configurations that do not come to a sharp peak. The areas 112 between the blades 110 can be configured to effectively transport the cut bone material proximally when the elongate body 104 is rotated. The symmetric and sharply peaked blades 110 shown in FIG. 2 are one example of a suitable configuration, and it will be understood that other configurations may also be used.

The elongate body 104 includes a coating, such as titanium nitride, disposed on a base material, such as stainless steel. In some examples, the base material is the material from which the elongate body 104 is molded or ground. In other examples, the base material may include one or more plated layers, such as nickel or chromium, between the molded or ground material and the coating. In this document, the term "base material" is intended to denote the material directly beneath the coating, so that if or when the coating is worn during use, the base material becomes visible.

The coating can be harder than the base material, which may increase the lifetime of the elongate body 104 beyond what would be achieved by a similarly-shaped elongate body formed solely from the base material. The coating can be a different color than the base material, so that a visual inspection of the femoral reamer 100 may readily indicate one or more areas or regions on the elongate body 104 where the coating has been worn away. In this manner, the coating may function as a wear indicator and may indicate to the practitioner that the femoral reamer 100 may need replacement or reworking Because the worn area may occur on a blade 110 or on an area 112 between adjacent blades, it is preferable that the coating extends over both the blades 110 and the areas 112 between the blades 110. The coating may preferably extend over the distal end 106 of the elongate body 104.

The thickness of the coating may be linked to a particular tolerance on the diameter of the drilled femoral canal. The tolerance may be determined by a particular configuration of a femoral stem to be implanted in the femoral canal. For instance, an example femoral reamer may be specified to drill a hole having a diameter between specified values L (for "low") and H (for "high"). Prior to use, the diameter of the femoral reamer is at the high end, H, of the specified range of hole diameters. In other words, the example femoral reamer, prior to use, may subtend a diameter of H when rotated around its longitudinal axis. As the coating wears down, the diameter subtended by the femoral reamer decreases from the high end of the specified range, H, to the low end of the specified range, L. At the end of its lifetime, the diameter of the femoral reamer is at the low end, L, of the specified range of hole diameters. In other words, the example femoral reamer, at the end of its lifetime, may subtend a diameter of L when rotated around its longitudinal axis. In this example, assuming that the coating wears out first on the blade, the coating on the example femoral reamer may have an initial thickness, T, equal to (H−L)/2. In other examples, with more complicated geometry, the coating may have another suitable value for its initial thickness. In these examples, the coating has a thickness that is related to a tolerance on the diameter of the hole to be drilled by the femoral reamer.

Figure 4:
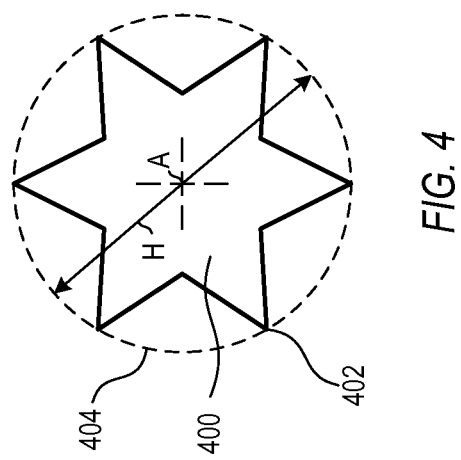
FIG. 4 is an end-on schematic drawing of a femoral reamer prior to use, in its initial wear stage.
Figure 3:
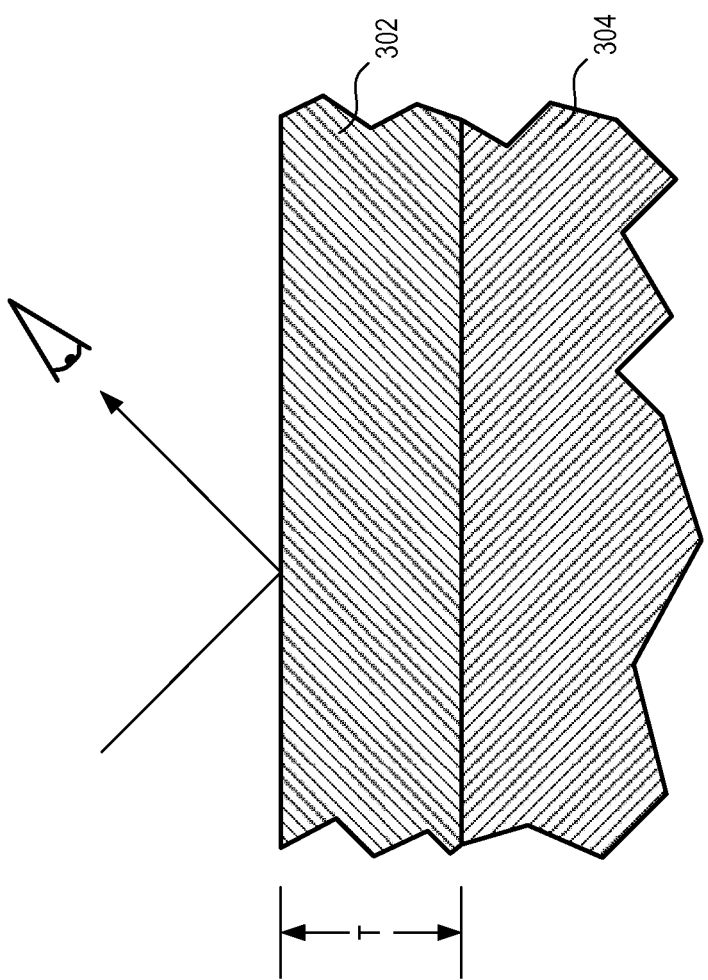
FIG. 3 is a side-view schematic drawing of a coating disposed on a base material of a femoral reamer prior to use, in its initial wear stage.
Figure 6:
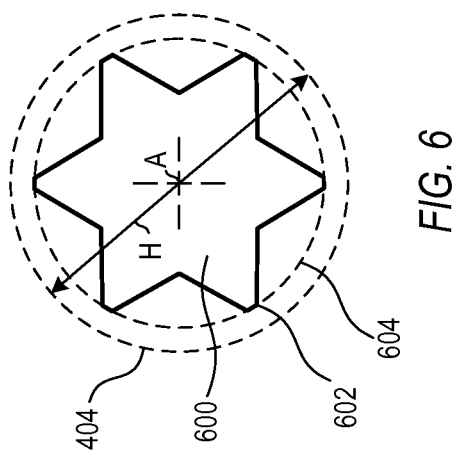
FIG. 6 is an end-on schematic drawing of a femoral reamer in an intermediate wear stage.
Figure 5:
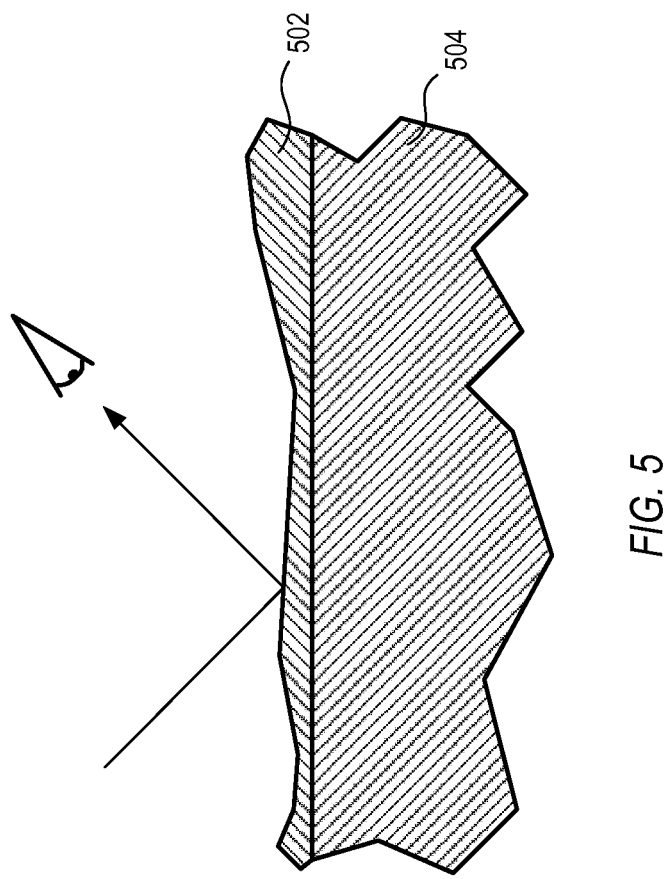
FIG. 5 is a side-view schematic drawing of a coating disposed on a base material of a femoral reamer in an intermediate wear stage.
Figure 8:
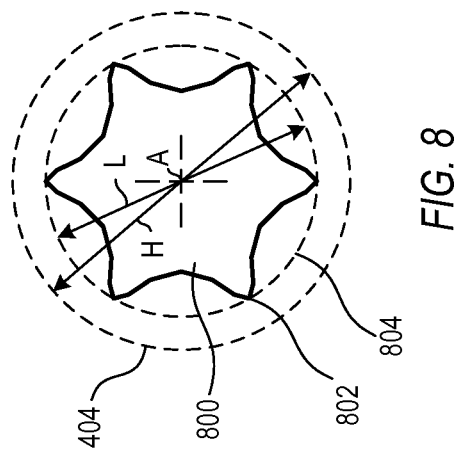
FIG. 8 is an end-on schematic drawing of a femoral reamer in a final wear stage.
Figure 7:
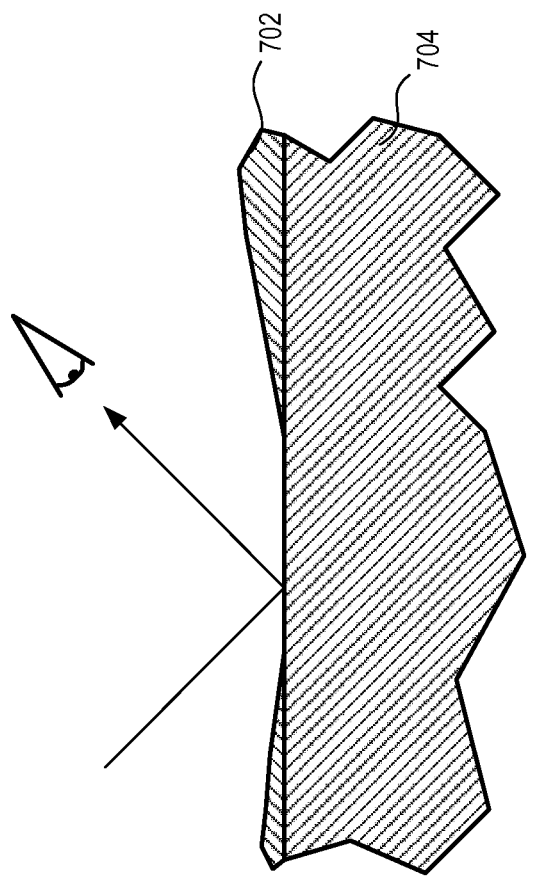
FIG. 7 is a side-view schematic drawing of a coating disposed on a base material of a femoral reamer in a final wear stage.

FIGS. 3, 5, and 7 show an example coating in initial, intermediate, and final wear stages, respectively. FIGS. 4, 6, and 8 show a femoral reamer in the corresponding initial, intermediate and final wear stages.

FIG. 3 is a side-view schematic drawing of a coating 302 disposed on a base material 304 of a femoral reamer prior to use, in its initial wear stage. In this example, the coating has a thickness T, which is related to a tolerance on the diameter of the hole to be drilled by the femoral reamer. As noted above, the base material 304 may be the material from which the elongate body is molded or ground or may be the topmost of one or more layers deposited on the material from which the elongate body is molded or ground. A practitioner looking at the femoral reamer sees only the color of the coating 302; the base material 304 is completely obscured.

FIG. 4 is an end-on schematic drawing of a femoral reamer 400 prior to use, in its initial wear stage. As the femoral reamer 400 is rotated around its longitudinal axis (A), the blade 402 subtends a diameter 404 denoted by H, where H represents a high end of a specified range of acceptable hole diameters.

FIG. 5 is a side-view schematic drawing of a coating 502 disposed on a base material 504 of a femoral reamer in an intermediate wear stage. The coating thickness is greater than zero at all the locations on the blades and the areas between the blades, but may be less than T at one or more of these locations. A practitioner looking at the femoral reamer sees only the color of the coating 502; the base material 504 is completely obscured.

FIG. 6 is an end-on schematic drawing of a femoral reamer 600 in an intermediate wear stage. As the femoral reamer 600 is rotated around its longitudinal axis (A), the blade 602 subtends a diameter 604 that is less than the initial diameter 404 denoted by H, but is still within a specified range of acceptable hole diameters.

FIG. 7 is a side-view schematic drawing of a coating 702 disposed on a base material 704 of a femoral reamer in a final wear stage. The coating thickness has decreased to zero at one or more locations on the blades and the areas between the blades. A practitioner looking at the femoral reamer sees the color of the base material 704 in the area or areas of wear, indicating that the femoral reamer is at the end of its lifetime and should be replaced or reworked.

FIG. 8 is an end-on schematic drawing of a femoral reamer 800 in a final wear stage. As the femoral reamer 800 is rotated around its longitudinal axis (A), the blade 802 subtends a diameter 804 denoted by L, where L represents a low end of a specified range of acceptable hole diameters. For some blade geometries, the initial thickness of the coating, T, is related to the high and low values in the range of acceptable hole diameters by $T=(H-L)/2$.

Figure 9:
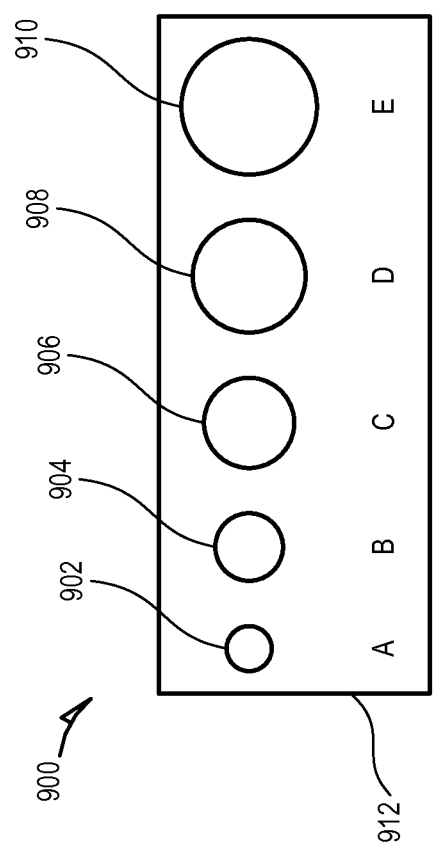
FIG. 9 is a top-view drawing of a kit of differently-sized femoral reamers.

FIG. 9 is a top-view drawing of a kit 900 of differently-sized femoral reamers 902, 904, 906, 908, 910. The kit 900 can include a housing 912, which can have holes or slots labeled with appropriate indicia, such as numbers or letters, that indicate which femoral reamer goes in which hole or slot. The indicia can correspond to particular femoral stem configurations. In some examples, a specified tolerance on the specified femoral canal size is different for at least two of the femoral stem configurations, and the coating thickness is different for at least two of the femoral reamers in the kit. In some examples, the base material is the same for all the femoral reamers in the kit. In some examples, the coating is the same material for all the femoral reamers in the kit.

FIG. 10 is a flow chart of an inspection method 1000 for a femoral reamer. The inspection method 1000 may be executed using the femoral reamer 100 of FIG. 1, or with another suitable femoral reamer. Step 1002 selects a femoral stem. Step 1004 specifies or identifies a range of suitable femoral canal sizes for the selected femoral stem. The manufacturer of the femoral stem may provide the range of suitable femoral canal sizes. The femoral canal sizes may be circular and require only a diameter for size specification, or may be elongated and require sizes in two dimensions for size specification. Additionally, for a tapered femoral stem, the femoral canal size may also specify a taper angle or other suitable dimension. Step 1006 selects a femoral reamer. In some examples, the femoral reamer is selected from a kit of differently-sized femoral reamers. The selected femoral reamer can be nominally sized to drill a femoral canal of a size within the specified or identified range of suitable femoral canal sizes. Step 1008 visually inspects the selected femoral reamer. If there is more than one color visible on the femoral reamer, then step 1010 observes at least one area or region on the selected femoral reamer in which a base material of the femoral reamer is visible through a coating on the femoral reamer. The base material and the coating can have different colors. If there is more than one color visible on the femoral reamer, then step 1016 determines, from the observed at least one area or region, that the femoral reamer has a size dimension (e.g., an outer diameter) that is outside the specified or identified range of femoral canal sizes. If there is more than one color visible on the femoral reamer, then step 1018 replaces the femoral reamer. If there is not more than one color visible on the femoral reamer, then step 1012 determines from the observed at least one area or region that the femoral reamer has diameter size dimension that is inside the specified or identified range of femoral canal sizes. If there is not more than one color visible on the femoral reamer, then step 1014 drills a femoral canal with the femoral reamer.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, kit, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A femoral reamer system, comprising:
a plurality of femoral reamers corresponding to a plurality of femoral stem configurations, each femoral stem configuration having an associated specified femoral canal size and a specified tolerance on the specified femoral canal size, each femoral reamer including a shaft, an elongate body disposed at a distal end of the shaft, and a plurality of blades disposed helically around an exterior of the elongate body, and each elongate body including a base material of a first color and a coating of a second, different color disposed on the base material, the coating being harder than the base material and having a thickness related to the specified tolerance on the specified femoral canal size.

2. The femoral reamer system of claim 1,
wherein the specified tolerance on the specified femoral canal size is different for at least two of the femoral stem configurations in the plurality; and
wherein the coating thickness is different for at least two of the femoral reamers in the plurality.

3. The femoral reamer system of claim 1,
wherein the base material is the same for each femoral reamer in the plurality; and
wherein the coating is the same material for each femoral reamer in the plurality.

4. The femoral reamer system of claim 1, wherein, for at least one of the plurality of femoral reamers, the thickness of the coating equals half the width of the specified tolerance on the specified femoral canal size.

5. The femoral reamer system of claim 1, wherein, for at least one of the plurality of femoral reamers, the coating is disposed over the plurality of blades and between adjacent blades in the plurality.

6. The femoral reamer system of claim 1, wherein, for at least one of the plurality of femoral reamers, each blade in the plurality extends less than a full revolution around the elongate body.

7. A method, comprising:
identifying a range of suitable femoral canal sizes for a selected femoral stem to be implanted;
selecting a femoral reamer including a base material of a first color and a coating of a second, different color disposed on the base material, the femoral reamer being nominally sized to drill a femoral canal of a size within the identified range of suitable femoral canal sizes;
visually inspecting the selected femoral reamer, including observing at least one region on the selected femoral reamer in which the first color of the base material is visible through the second color of the coating; and
determining, from the observed at least one region, that the selected femoral reamer has a size dimension that is outside the identified range of suitable femoral canal sizes.

8. The method of claim 7, wherein selecting the femoral reamer includes selecting a femoral reamer including a coating having a thickness related to the identified range of suitable femoral canal sizes.

9. The method of claim 7, wherein selecting the femoral reamer includes selecting a femoral reamer including a coating having a thickness equal to half of a width of the identified range of suitable femoral canal sizes.

10. The method of claim 7, wherein selecting the femoral reamer includes selecting a femoral reamer including a coating that is harder than the base material.

11. The method of claim 7, wherein selecting the femoral reamer includes selecting a desired combination of a shaft, an elongate body disposed at a distal end of the shaft, and a plurality of blades disposed helically around an exterior of the elongate body.

12. The method of claim 11, wherein selecting the desired combination includes selecting a plurality of blades that extend less than a full revolution around the elongate body.

13. The method of claim 11, wherein selecting the desired combination includes selecting a plurality of blades having the coating disposed over an outer blade surface and between adjacent blades in the plurality.

14. A method, comprising:
selecting a femoral stem to be implanted;
identifying a range of suitable femoral canal sizes for the selected femoral stem;
selecting a femoral reamer, from a kit of differently-sized femoral reamers, including a base material of a first color and a coating of a second, different color disposed on the base material, the selected femoral reamer being nominally sized to drill a femoral canal of a size within the identified range of suitable femoral canal sizes;
visually inspecting the selected femoral reamer;
observing at least one area on the selected femoral reamer in which the base material of the femoral reamer is visible through the coating on the femoral reamer; and
determining, from the observed at least one area, that the selected femoral reamer has a size dimension that is outside the identified range of suitable femoral canal sizes.

15. The method of claim 14, wherein selecting the femoral reamer includes selecting a femoral reamer including a coating having a thickness related to the identified range of suitable femoral canal sizes.

16. The method of claim 14, wherein selecting the femoral reamer includes selecting a femoral reamer including a coating having a thickness equal to half of a width of the identified range of suitable femoral canal sizes.

17. The method of claim 14, wherein selecting the femoral reamer includes selecting a femoral reamer including a coating that is harder than the base material.

18. The method of claim 14, wherein selecting the femoral reamer includes selecting a desired combination of a shaft, an elongate body disposed at a distal end of the shaft, and a plurality of blades disposed helically around an exterior of the elongate body.

19. The method of claim 18, wherein selecting the desired combination includes selecting a plurality of blades that extend less than a full revolution around the elongate body.

20. The method of claim 18, wherein selecting the desired combination includes selecting a plurality of blades having the coating disposed over an outer blade surface and between adjacent blades in the plurality.

* * * * *

UNITED STATES PATENT AND TRADEMARK OFFICE
CERTIFICATE OF CORRECTION

PATENT NO. : 9,451,969 B2
APPLICATION NO. : 14/787850
DATED : September 27, 2016
INVENTOR(S) : Borries et al.

It is certified that error appears in the above-identified patent and that said Letters Patent is hereby corrected as shown below:

In the Claims

In Column 9, Line 16, in Claim 3, delete "claim 1 ," and insert --claim 1,--, therefor In Column 9, Line 53, in Claim 9, delete "claim 7 ," and insert --claim 7,--, therefor In Column 10, Line 1, in Claim 10, delete "claim 7 ," and insert --claim 7,--, therefor Signed and Sealed this
Twentieth Day of March, 2018

Andrei Iancu
*Director of the United States Patent and Trademark Office*